US012636429B2

(12) United States Patent
Richter et al.

(10) Patent No.: US 12,636,429 B2
(45) Date of Patent: May 26, 2026

(54) DRUG DELIVERY SYSTEM

(71) Applicant: Fraunhofer-Gesellschaft zur Foerderung der angewandten Forschung e.V., Munich (DE)

(72) Inventors: Martin Richter, Munich (DE); Thomas Thalhofer, Munich (DE); Lorenz Gruenerbel, Munich (DE)

(73) Assignee: Fraunhofer-Gesellschaft zur Foerderung der angewandten Forschung e.V., Munich (DE)

( * ) Notice: Subject to any disclaimer, the term of this patent is extended or adjusted under 35 U.S.C. 154(b) by 667 days.

(21) Appl. No.: 18/070,274

(22) Filed: Nov. 28, 2022

(65) Prior Publication Data

US 2023/0096689 A1      Mar. 30, 2023

Related U.S. Application Data

(63) Continuation of application No. PCT/EP2020/064594, filed on May 26, 2020.

(51) Int. Cl.
    *A61M 5/142*          (2006.01)
    *A61M 5/168*          (2006.01)

(52) U.S. Cl.
    CPC .... *A61M 5/14248* (2013.01); *A61M 5/16836* (2013.01); *A61M 2005/14252* (2013.01)

(58) Field of Classification Search
    CPC ............................... F04B 45/00; F04B 45/047
    See application file for complete search history.

(56) References Cited

U.S. PATENT DOCUMENTS

| 4,311,050 | A | 1/1982 | Bessman |
| 4,734,092 | A | 3/1988 | Millerd |
| 6,910,377 | B1 | 6/2005 | Richter et al. |
| 7,896,865 | B2 | 3/2011 | Kulessa |
| 8,382,452 | B2 | 2/2013 | Richter et al. |
| 2005/0070875 | A1 | 3/2005 | Kulessa |
| 2009/0259176 | A1 | 10/2009 | Yairi |
| 2010/0121257 | A1 | 5/2010 | King |
| 2010/0290935 | A1 | 11/2010 | Richter et al. |
| 2011/0066108 | A1 | 3/2011 | Geipel et al. |
| 2013/0183209 | A1 | 7/2013 | Richter et al. |
| 2013/0237955 | A1 | 9/2013 | Neta et al. |
| 2018/0117296 | A1 | 5/2018 | Damiano et al. |

(Continued)

FOREIGN PATENT DOCUMENTS

| CN | 103249486 | A | 8/2013 |
| CN | 209137590 | U | 7/2019 |
| EP | 1320727 | B1 | 8/2005 |

(Continued)

OTHER PUBLICATIONS

EMI Analyst Software, "Coplanar Capacitance", https://www.emisoftware.com/calculator/coplanar-capacitance.

(Continued)

*Primary Examiner* — Laura A Bouchelle
(74) *Attorney, Agent, or Firm* — Perkins Coie LLP; Michael A. Glenn

(57)          ABSTRACT

Drug delivery system including: a reservoir having a meander shape or spiral shape, the reservoir including an inlet and a filter; a capacitance measurement device configured to determine a parameter of the reservoir; and a micropump configured to deliver a fluid from the reservoir to an outlet.

14 Claims, 5 Drawing Sheets

10'

(56) References Cited

U.S. PATENT DOCUMENTS

2018/0272058 A1    9/2018  Pizzochero et al.

FOREIGN PATENT DOCUMENTS

| | | | |
|---|---|---|---|
| EP | 2295096 | A1 | 3/2011 |
| JP | 2005103273 | A | 4/2005 |
| JP | 4846221 | B2 | 10/2011 |
| JP | 2013543447 | A | 12/2013 |
| JP | 2018525060 | A | 9/2018 |
| WO | 2008142640 | A1 | 11/2008 |
| WO | 2009149367 | A1 | 12/2009 |
| WO | 2011107162 | A1 | 9/2011 |
| WO | 2012031630 | A1 | 3/2012 |
| WO | 2019186375 | A1 | 10/2019 |

OTHER PUBLICATIONS

Nassr, Amr A, et al., "(Abstract) Coplanar capacitance sensors for detecting water intrusion in compositestructures", Measurement Science and Technology, vol. 19, No. 7, IOP Publishing Ltd.; https://www.iopscience.iop.org/article/10.1088/0957-0233/19/7/075702, Jun. 12, 2008, 3 pp.

DRUG DELIVERY SYSTEM

CROSS-REFERENCE TO RELATED APPLICATION

This application is a continuation of copending International Application No. PCT/EP2020/064594, filed May 26, 2020, which is incorporated herein by reference in its entirety.

BACKGROUND OF THE INVENTION

Embodiments of the present invention refer to a drug delivery system.

There are many medical applications which need regular small quantities of drugs or agents to be delivered in the body, e.g.:

Diabetes patients, who need Insulin to keep the blood sugar level at a healthy level Hormone therapy Pain therapy Therapy of Parkinson Infusion for premature infants Nuclear medicine (dosing of nuclear marker)

But also new therapies like the dosing of monoclonal antibodies for the therapy of different cancer diseases, arthritis, rheuma, multiple sclerosis, Alzheimer's, megrim, etc.

Most of these applications are subcutaneous drug delivery, some of them are intravenous infusion.

There are some patents/patent applications mentioned in the context of drug delivery systems: These are EP 1 320 727 B1 describing an fluid reservoir with measurement of fluid level by capacitance measurement, U.S. Pat. No. 8,382,452, describing a safety valve, and WO 2011/107162 A1 describing a bending transducer.

Below, the general conventional technology, e.g., in the context of therapy of diabetes will be discussed. There are several possibilities to does insulin subcutaneously:

1. Syringes or pens: the patient has to injure his skin several times a day
2. Tethered pump: portable pumps, on the market since the early 90's. The pump is in a bag at the body, the insulin is delivered to the body with a catheter. The Insulin glass reservoir can be replaced if empty, the rest of the pump is reusable. Market leader is Metronic.
3. Patch pumps: on the market for about 10 years, the whole pump system is disposable for a three-day use, it can be attached to the body like a patch. Market leader is Insuled with the Omnipod pump.

The use of pump systems has some benefits compared to the pen technology:

Much less pinholing to the skin, less pain to the patients

The delivery of insulin can be controlled and adapted to the specific needs of the patients The pump system can be connected to a glucose sensor system, which is monitoring the glucose level continuously. With that, a closed loop control of the glucose level can be achieved Beside Insulin, also other agents to increase the glucose level can be delivered by the pump system Although there are many advantages, there are also disadvantages:

The use of a pump cannot be hidden from other people, especially in summertime, which might have some social impact, with potential to stigmatize the patients.

Although the use of patch pumps has advantages, the use of pens is state of the art to treat patients in Europe, it is the standard treatment for diabetes patients. The reason is mainly, that the cost of patch pumps is much higher compared to the pen technology.

If a patch pump would be available, which is on the one side miniaturized, accurate and safe, and has on the other side the potential to be cost efficient in mass production, it would be likely the standard therapy of diabetes. But there are some challenges to meet that goal.

The use of a silicon MEMS pump for diabetes can be considered as an promising approach. However, Debiotech (CH) focused to this approach (using a silicon MEMS pump for insulin delivery) continuously since about 25 years without a market breakthrough up to now.

In current patch pumps, the size limitations are given on the one hand by the pump system (piston pump technology), and the on the other hand, by the volume of the reservoir. Therefore, there is a need for an improved approach.

An objective of the present invention is to provide a drug delivery system enabling to dose drugs like insulin or in general fluids in a manner having an improve trade-off regarding usability, accuracy of the delivered fluid and cost efficiency.

SUMMARY

An embodiment may have a drug delivery system comprising: at least one reservoir comprising a meander shape or spiral shape, the reservoir comprising an inlet and a filter; a measurement device configured to determine a parameter of the at least one reservoir; and at least one micropump configured to deliver a fluid from the reservoir to an outlet; wherein the filter is arranged at the inlet and configured to allow air flowing into the reservoir when the fluid is delivered out of the reservoir; wherein the measurement device is implemented as capacitance measurement device comprising two electrodes arranged with the reservoir inbetween, wherein the reservoir and/or a fluid within the reservoir acts as a dielectricum; wherein the capacitance measurement device is configured to determine a dielectric constant and/or capacity, wherein the dielectric constant, wherein the capacity is dependent on a fluid level of the reservoir; wherein comprising a control configured to determine the fluid level based on a capacitance signal determined by the capacitance measurement device; wherein the control is configured to detect using the capacitance signal determined by the capacitance measurement device at least one of the following: catheter blockage, pump failure or glass break.

An embodiment provides a drug delivery system comprising a reservoir having inlet and a filter. The reservoir may, for example, prefilled with drug/fluid. The system further comprises a measurement device, e.g. a capacitance measurement device, and a micropump. The reservoir advantageously has a meander shape or a spiral shape. The micropump is configured to deliver a fluid, like a drug, from the reservoir to the outlet. The filter is arranged at the inlet and configured to allow air flowing into the reservoir when the fluid is delivered out of the reservoir.

Embodiments of the present invention are based on the finding that a reservoir, e.g., a reservoir having a meander shape, can be coupled to a capacitance measurement device enabling an improved controlling of same. The combination of a capacitive dose monitoring method, which fits perfectly to the micropump and enables to detect one single pump stroke with a sufficient resolution improves the accuracy by delivering the drug significantly. In other words this means that two main innovations make the difference, When compared to the conventional technology, namely a dosing monitoring and micropump design.

According to embodiments a combination of a new micropump technology with a novel, accurate and cost efficient dosing monitoring technology is provided. The dosing monitoring technology can, for example, not only resolve every single pump stroke of 25 nl, but can also address safety and reliability topics like catheter blockage, bubble recognition, pump failure, reservoir fracture, fluid level detection of the reservoir According to embodiments the superior micropump design enables higher compression ratios, smaller stroke volumes, smaller chip size, better bubble tolerance, smaller capillary sticking, smaller van der Waals sticking, and integrated free flow stop.

As the stroke volume of micro actuator usually is small, and the dead volume of the pump chamber is large, the compression ratio (equivalent to the ratio between stroke volume to dead volume) of piezo-driven micropump is small, too. One hurdle is the nature of piezo physics, as 80% of the stroke is performed "downwards" by the positive voltage, as negative voltage stroke is limited by depolarisation of the piezo. For that, a huge dead volume and with it a small compression ratio remains at "conventional" piezo-driven micropumps. A huge step in micropump performance has been achieved by the Fraunhofer micropump team, here the piezo effect is used during the gluing step to the silicon chip: after placement a high voltage is applied to the piezo during hardening, and released after the glue is hard: as a result the piezo is pretensioned in a defined way "upwards", if the voltage is released. Consequently, the pump chamber height was reduced to a very small value, and the great reduction of the dead volume enables micropumps with either very large compression ratios, or miniaturization to a very small chip size.

Due to the highly accurate and small stroke volume the drug delivery system profits from another advantage: The standard insulin on the market is U100 (that means 100 units in one milliliter), which is also used in most patch pumps. 3 ml of U100 insulin is enough for about 3 days. The low concentration of U100 limits also the size of the patch pump. Currently, there are also higher concentrated Insulin available or under development, e.g. U400, U500, or even U1000. For a U1000 Insulin (1000 units in one ml), which has a 10 times higher concentration compared to U100, the drug volume can be reduced by a factor of 10. A 0.3 ml reservoir volume of U1000 is enough for 3 days, where a 1 ml reservoir is can deliver 10 days to the patients.

For example, every single pump stroke of, for example, 25 nanoliter can be detected or monitored. Due to the combination of a reservoir technology and a micropump from the drugs having high concentrations, e.g., a highly concentrated insulin, can be used, so that the volume of the reservoir can be reduced. Background thereof is that the introduction of a micropump system enables to deliver volumes that are smaller than the typical 20 or 25 nanoliter (which is about than ¼₀ of 1 insulin unit of U1000. Furthermore, the micropump system is so small that it does not contribute significantly to the size (especially thickness of a patch pump). Therefore, the entire drug delivery system can be designed very small and ultra-flat. Since the drug delivery system can consist of a reservoir having an inlet, a capacitance measurement device and a micropump, it consists of only few parts, so that the complexity and the expected production costs are low.

According to embodiments, the drug delivery system can comprise a needle attached to the micropump. An advantage of the combination of a needle to the patch pump system is that the needle is very close to the micropump, which has no elastic elements and thus, avoiding problems that occur with tubing's at small dosing volumes. According to embodiments, the micropump can be arranged at the end of the meander shaped reservoir or in the middle of the spiral shaped reservoir enabling a very compact design of the entire drug delivery system.

According to embodiments, the reservoir can be prefilled, e.g., by a high concentrated insulin. An exchangeable reservoir or completely exchangeable drug dosing system can be designed very cost efficiently. The usage of a spiral shape or meander shape for starting the fluid volume enables that an entire reservoir can be filled from one end of the meander track or the spiral track. When considering that during the delivery of the fluid the reservoir becomes empty and the fluid is replaced by air, the meandering/spiral shape enables that just a small portion at the inlet is in contact with the air, so that the fluid is not contaminated due to the air contact. By use of the inlet, it is advantageously possible that no negative pressure is generated. Furthermore, when ensuring that the reservoir/drug delivery system is exchanged, e.g., when 90% of the liquid is delivered, the very small portion which was in contact with the air is not delivered to the patient. The capacitance measurement device enables beneficially to monitor the fluid level within the reservoir. Note that according to embodiments the reservoir may be made out of glass or a polymer enabling to monitor the fluid level by the capacitance measurement device.

According to embodiments, the filter is arranged at the inlet and configured to allow air flowing into the reservoir when the fluid is delivered out of the reservoir. According to embodiments, the filter comprises a hydrophobic filter (fluid filter avoiding intrusion of fluids (e.g. during the shower) or an activated carbon filter (gas filter+bacteria filter) or a hydrophobic filter and an activated carbon filter arranged in series. Also other filter types or combination of other filter types (e.g. having two or three or more barriers) are possible. For example, as a filter a passive membrane or mesh can be used, ideally with very small (0.2 μm) pore size to ensure sterile filtration of the incoming air. Additionally, the filter can contain materials such as activated carbon for further elimination of impurities in the incoming gas. The filter may be in contact with the drug contained in the reservoir and therefore has to be compatible with this drug, at least for the filter most inside. Also a combination of three filters is possible, e.g. a hydrophobic filter outside, a bacteria filter inside and a gas filter in the middle). The inner filter may be in contact with the fluid and may avoid the contact of the fluid and the other filters. The usage of a filter is advantageous, since it enables to protect the fluid in the reservoir from the contaminated air intruding though the inlet of the reservoir. Note the described system having a reservoir with an inlet is uncommon. According to embodiments, the inlet may comprise a sealing enabling to close the inlet, before the pump is attached to the body and used for the first time. The one or more filters enabled to avoid the contamination, e.g., by bacteria or viruses from the fluid. The optional sealing can provide another variant, which can be opened manually (e.g. for the first use). According to embodiments, the capacitance measurement device enables to determine the status of the inlet (opened or closed). Note, the filter may be designed to maintain an external pressure (e.g. during diving).

According to embodiments, the measurement device may be a capacitance measurement device which is configured to determine a dielectric constant and/or capacity; the dielectric constant and/or the capacity is, for example, dependent on a fluid level of the reservoir. According to embodiments, the system comprises a control configured to determine the fluid level based on a capacitance signal (change of the capacitance signal) determined by the capacitance measurement device.

Another possibility to detect the meniscus level in the meander shaped reservoir could be optical sensor or resistive or magnetic measurement. Thus the measurement device may be implanted by use of optical means. However, the capacitance measurement would be the most accurate and cost efficient method.

According to embodiments, the system comprises a control which is configured to determine a stroke volume during the operation of the micropump (pumping using one or more strokes) based on a capacitance signal determined by the capacitance measurement device or based on a change of the fluid level of the reservoir, said fluidic level is monitorable using the capacitance signal.

According to embodiments, the system comprises a control which is configured to determine a disturbance within the reservoir, e.g. detecting intrusions, or a disturbance of the micropump or a disturbance of the drug delivery system, e.g. needle dislocation, catheter blockage or to detect an open inlet.

According to embodiments, the capacitance measurement device comprises a third electrode which is, for example, attachable to the skin in order to recognize if the drug delivery system is correctly attached (to the skin); alternatively, the capacitance measurement device further comprises a electrode having two or more portions which may arranged before and/or behind the micropump in order to distinguish between drug and bubble/air/particle and fluid or an empty reservoir. Thus, according to embodiments, each of the two electrodes is separated into two or more portions.

According to embodiments, the stroke volume is detected by determining the fluid change during operation of the pump (during one or more pump strokes). If the volume changes/decreases without operation of the pump it can be concluded that there is leaking of the reservoir (16) or evaporation from the reservoir. If the volume increases it might be concluded that there is an reflow (from the body to the reservoir).

Thus, it is beneficial to use the capacitance measurement devices enabling to monitor the fluid level, a stroke volume or a disturbance. Expressed in other words, this means that the capacitance measurement device provides a multi-functional measurement device for the drug delivery system and can be produced in a cost efficient manner.

BRIEF DESCRIPTION OF THE DRAWINGS

Embodiments of the present invention will be detailed subsequently referring to the appended drawings, in which.

6

Figures 4A, 4B:
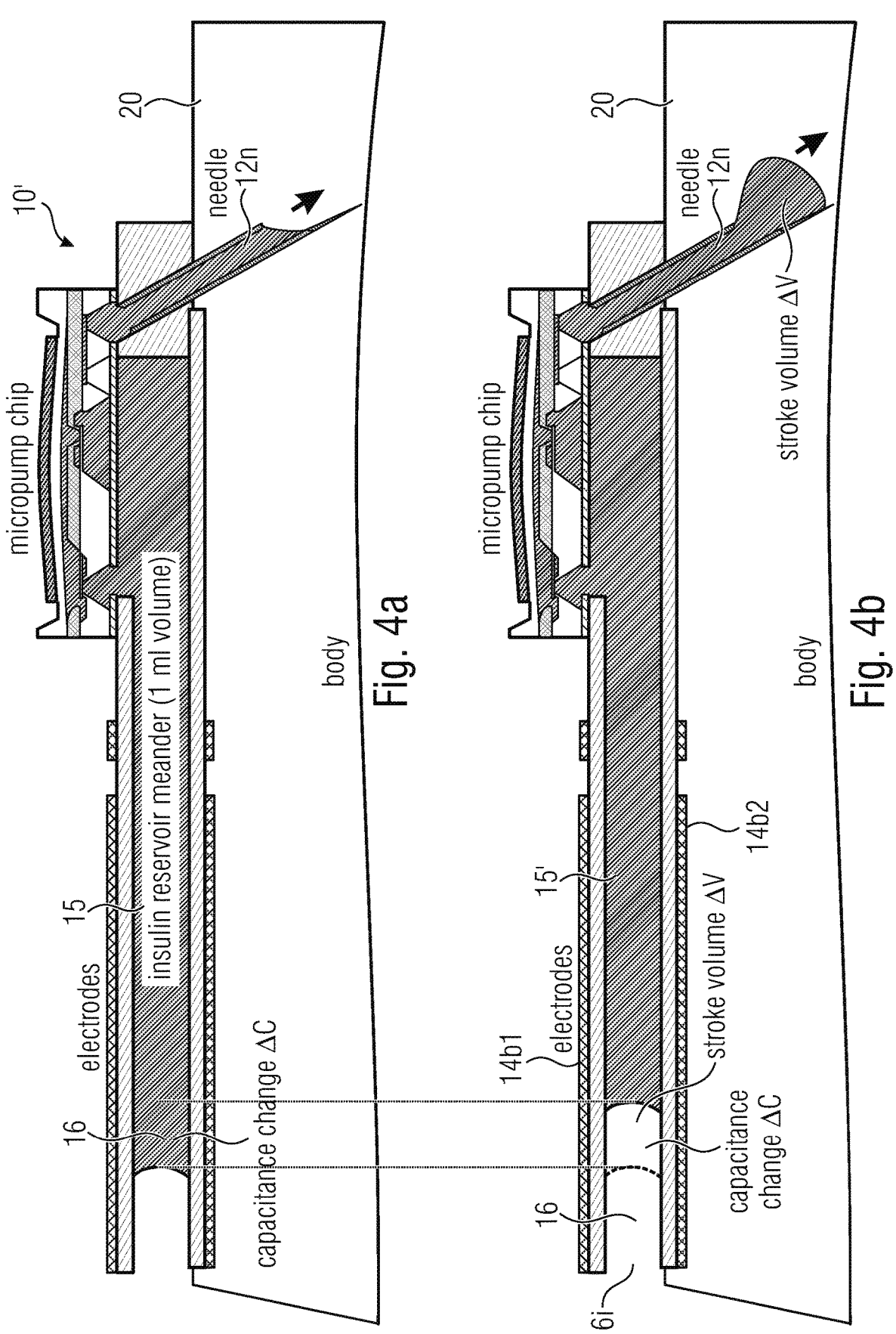
Figures 5A, 5B:
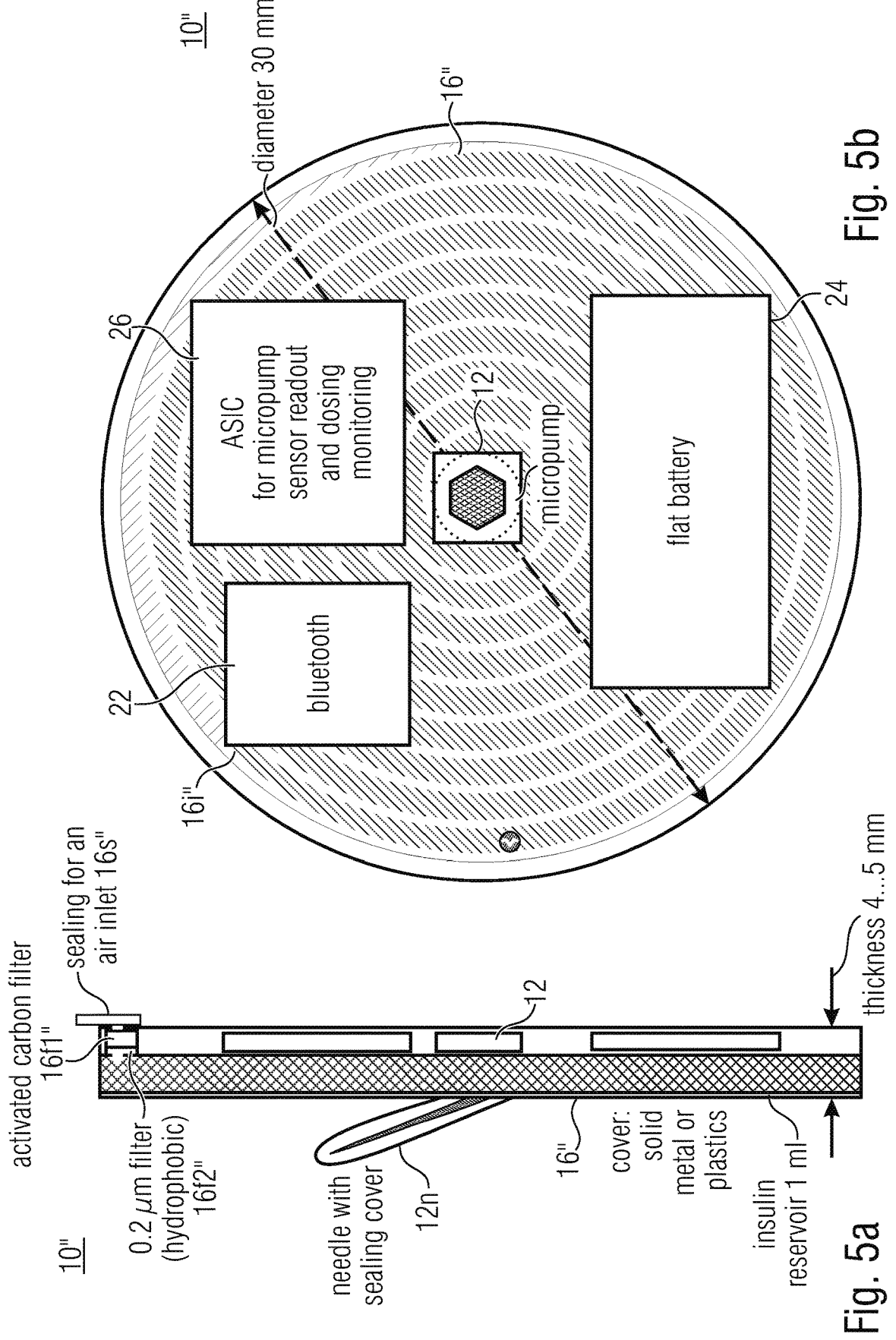

FIGS. 4a and 4b show a schematic cross section of a drug delivery system for illustrating the principle of the capacitance measurement device in more detail according to embodiments; and FIGS. 5a and 5b show a schematic illustration of a drug delivery system according to a further enhanced embodiment.

DETAILED DESCRIPTION OF THE INVENTION

Below, embodiments of the present invention will subsequently be discussed referring to the enclosed figures, wherein identical reference numbers are provided to objects having an identical or similar function, so that the description thereof is interchangeable and mutually applicable.

Before discussing embodiments of the present invention, an excursus to direct concentrations is given providing the possibility to use high concentrated drugs in a low volume instead of low concentrated drugs in a high volume. The excursus is discussed in the context of insulin, but is also valid for other drugs/fluids. This excursus is given, since a reduced volume for a reservoir enables to reduce the size of a drug delivery system. However, the usage of high concentrated volumes also leads to the need to accurately monitor the volume stroke when lowering the fluid/drugs into the basic need for delivering the fluid/drug in a very small and/or accurate volume.

In current patch pumps, the size limitation is given on the one hand by the pump system (piston pump technology), and on the other hand side by the volume of the reservoir:

The standard concentration of Insulin is U100. That means 100 units are within one milliliter. A reservoir of 3 milliliters of U100 insulin is needed for the treatment of about 3 days of a patch pump. Furthermore, there are high concentrated insulin types available or in development (up to U500 or U1000). A three ml reservoir of U1000 would be sufficient for 30 days of treatment, and a 1 ml reservoir of U1000 will enough for 10 days of treatment.

With that, a patch pump with a high concentrated insulin and an extremely miniaturized pump would be very advantageous for the patient, however, there are some challenges:

A U1000 insulin has a volume of 1 μl (according to $\frac{1}{1000}$ ml, according to 1 mm$^3$) for one insulin unit. However, the use of a U1000 insulin would need a pump system with an exemplary resolution of about $\frac{1}{40}$ of one unit, that means a volume resolution of 25 Nanoliter. Current piston pumps, which are cost efficient enough to be integrated in a disposable patch pump, are hardly able to have a volume resolution of 25 nanoliter (which is $\frac{1}{40}$ of 1 mm$^3$).

Next, if a pump system would be able to dose a volume of 25 nanoliter, there is no dosing monitoring technology available to control that this volume is dosed.

Next, long tubing lengths of some centimeter between tethered pumps and needle generate additional dosing error, as the fluidic capacitance of the weak components of the tubing or the presence of small gas bubble between pump and patient could generate a huge dosing error, if such small volumes are dosed by the pump.

The conclusion is that in case it is possible to deliver a fluid/drug in a small volume and to accurately monitor same, high concentrated drugs/volumes can be used so that it is possible to reduce the volume of the reservoir. As will be discussed with respect to FIG. 1, the micropump 12 of the drug delivery system 10 and the capacitance measurement device 14 of the drug delivery stems 10 provides a respective basis.

Figure 1:
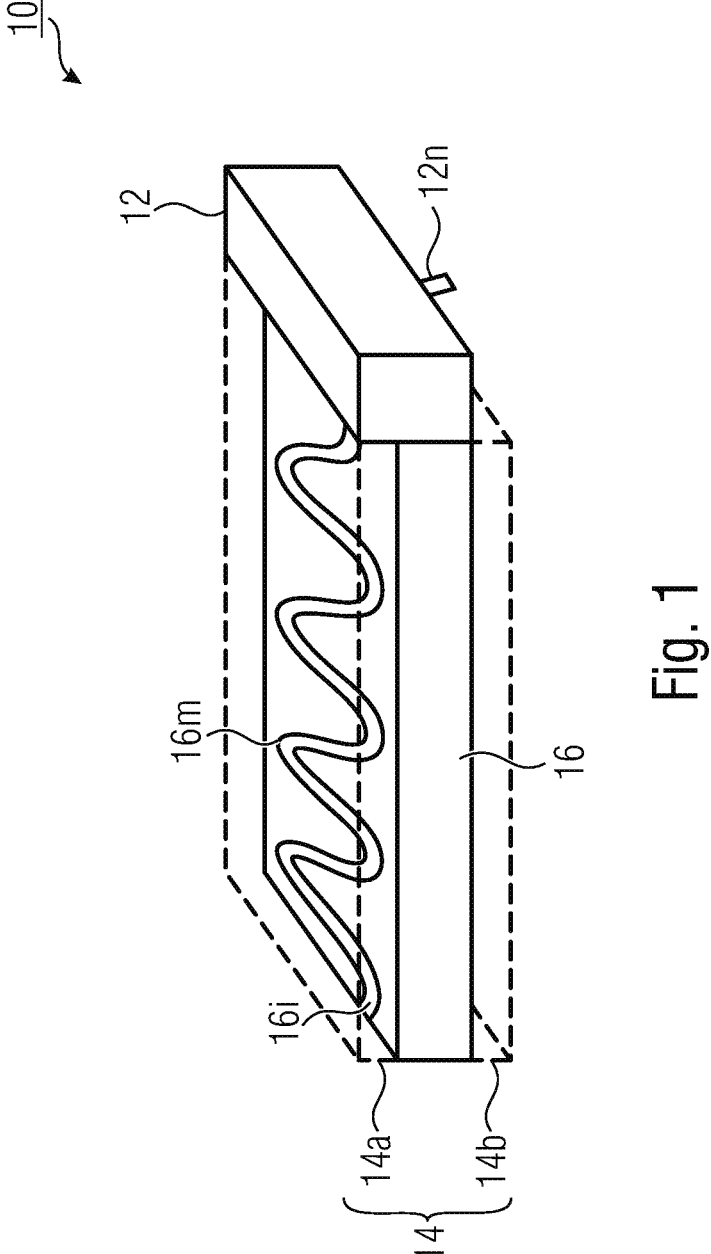
FIG. 1 shows a schematic block diagram of a drug delivery system according to basic embodiments.

FIG. 1 shows a drug delivery system 10 comprising a reservoir 16 and a micropump 12. Within the reservoir 16, a fluid, e.g., insulin (not shown) may be stored that can be dispensed by use of the micropump 12. For this, the micropump 12 can comprise at its outlet an optional needle 12n. within the reservoir 16, the fluid is stored within a meander 16m. This meander 16m extends from the inlet 16i of the reservoir 16 to the micropump 12.

The drug delivery system 10 further comprises the capacitance measurement device 14. Here, this device 14 is formed by two electrodes 14a and 14b. The electrode 14a is arranged on a topside (first main surface) of the (flat) reservoir 16, wherein the electrode 14b is arranged on the bottom side (second main surface opposite to the first main surface) of the reservoir 16. Due to this arrangement, the reservoir 16 forms a dielectric of the capacity 14a+14b. The dielectricity constant and thus, the capacity of the capacitor 14a+14b depend on the fluid within the reservoir 16 or the meander 16m. Thus, this principle enables to determine the fluid level within the meander 16m. Another possibility is that the change of the fluid level and thus, the stroke of the micropump 12 delivering the drug can be monitored by use of the capacitance measurement device 14. The elongated reservoir volume due the meander 16m forms a large area extending along the main surfaces of the reservoir 16. The area and especially the material properties in this area (between the electrodes 14a and 14b) have a large influence to the dielectricity constant of the capacitor and, thus, to the capacity formed by the electrodes 14a and 14b. The dielectricity constant and the capacity, respectively is dependent on the presence/amount of the fluid in the meander 16m. This configuration enables to resolute a capacity change due to the fluid level change quite good. For example, this arrangement enables to determine a volume change, e.g., due to a stroke of one microliter or smaller. Furthermore, according to embodiments, an additional disturbance detection mechanism can be used, for example, for detecting intrusions and needle dislocation. For example, a de-connection of the needle can result in less bag pressure and thus, less stroke, which can be monitored by the above-discussed capacitance system 14.

As discussed above, the meander 16m extends from the index 16i to the micropump 12. The inlet 16i has a purpose to allow the fluid flowing into the meander within which it is stored. Furthermore, it enables to allow air increasing into meander 16m, when a fluid out of the reservoir 16 is taken, e.g., by use of the micropump 12, when it delivers the fluid. In order to avoid bacteria or viruses coming in, a filter can be arranged in the inlet 16i. The filter can have small pore sizes. According to embodiments, the filter can be a hydrophobic filter or activated carbon filter. According to further embodiments, a combination of two filters, e.g., of a hydrophobic filter and activated carbon filter can be used. These two filters can be arranged in series. Of course, it is possible that according to further embodiments, other filter types configured to filter bacteria or viruses can be used. Additive to the filter a sealing can be provided at the inlet. Such a sealing prevents the intrusion of bacteria or viruses. However, it also prevents the intake of air, e.g., when fluid out of the reservoir 16 should be dispensed by use of the micropump 12.

Note, the capacitance measurement device may according to further embodiments comprise just one electrode attached to the reservoir, wherein e.g the skin is used as counter electrode in order to determine the dielectricity constant (change).

Below, taking reference to FIG. 2, optional features according to embodiments will be discussed.

Figure 2:
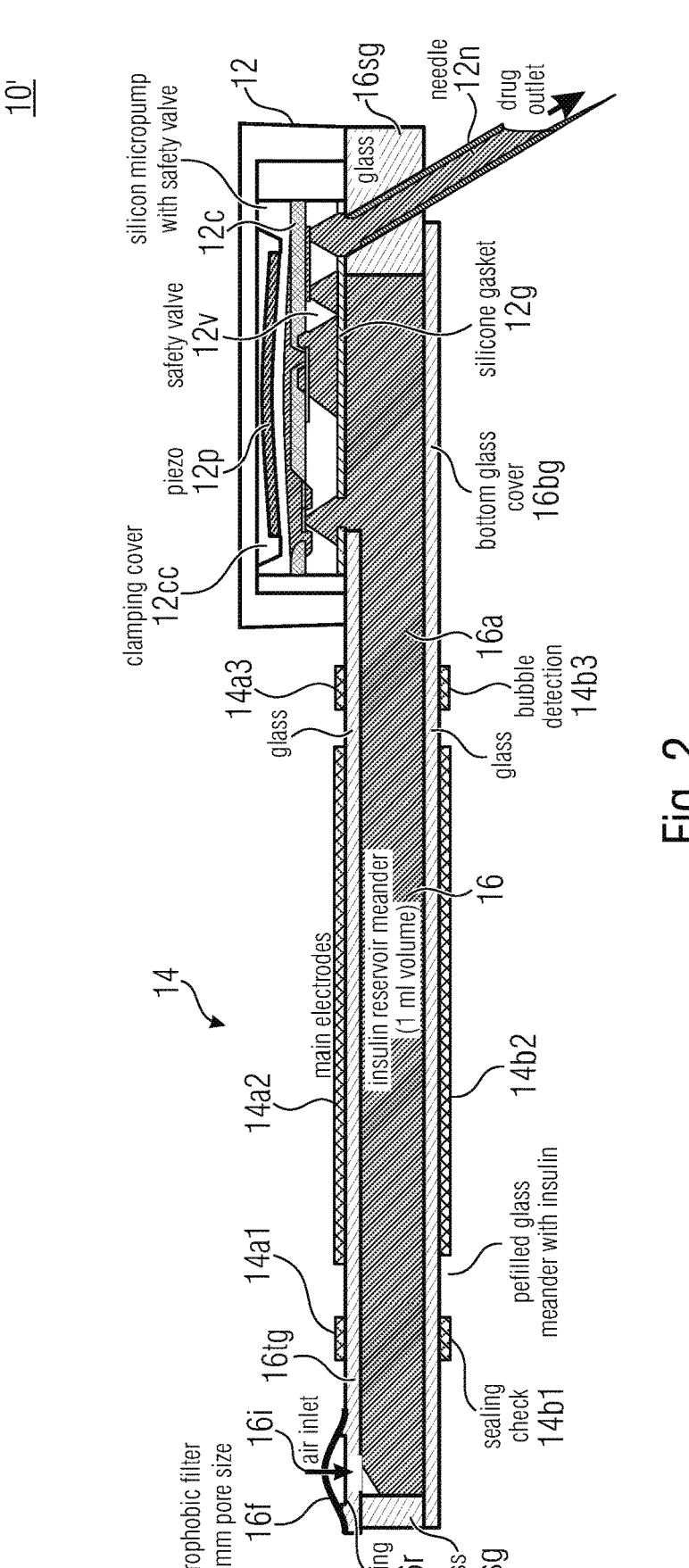
FIG. 2 shows a schematic cross section of a drug delivery system according to enhanced embodiments.

FIG. 2 shows a drug delivery system 10', e.g., used as diabetes patch pump. The system comprises the reservoir 16, the micropump 12 and electrode portions 14a1, 14a2 and 14a3 as well as 14b1, 14b2 and 14b3. These electrode portions 14a1 to 14b3 form the capacitance measurement device 14.

At the inlet 16i, a sealing 16s and a filter 16f are arranged. Here, it is, for example, a hydrophobic filter having a pore size of 0.1 μm implemented.

At the outlet of the pump 12 a needle 12n is arranged enabling the drug outlet. This needle 12n is directed attached to the patch 16+12. Below, the function of the micropump will be discussed. The micropump can be a silicone micropump (3.5×3.5 mm2) developing an airbag pressure larger than 30 kPa. For this, the pump 12 comprises a pump chamber 12c, which is activated using a piezoactuator 12p. At the outlet, a so-called safety value 12v can be arranged. Of course, it is possible that further valves, e.g., at the inlet and the outlet can be arranged. The entire pump 12 is covered by a clamping cover 12 cc concealed by a silicone gasket 12g. this pump entity 12 may be arranged on the topside of the reservoir 16.

The reservoir 16 may be manufactured out of a glass, i.e., comprising a bottom glass, 16bg and a top glass, 16tg. At the sides the reservoir 16 may be closed by glass elements 16sg. The use of glass is advantageous, since it has no significant influence to the capacitance measurement device 14. Alternatively, plastic or another non-conducting material may be used. On the top glass, 16tg the pump 12 may be arranged, wherein the silicone gasket 12g connects the two elements 16 and 12. The needle 12n may be fixed by use of the glass side element 16sg.

It should be noted that according to embodiments, the inlet 16i with the elements 16s and 16f may be arranged on the one hand of the reservoir 16, while the pump and the needle 12n may be arranged on the other hand. This enables to have a long trek within the reservoir 16, e.g., having the shape of a meander this trek and especially the fluid level within the reservoir 16 can be monitored by use of the capacitance measurement device 14. Here in this embodiment, the capacitance measurement device comprises three periods of electrodes first pair 14a1 and 14b1 for a sealing check. Main electrodes 14a1 and 14b2 for monitoring the fluid level and a third pair 14a3 and 14b3 fluid level detection.

The structure of the drug delivery system 10' has been discussed, the function principle of the system 10' and the components will be discussed.

If the micropump 12 is operated and makes a single stroke volume (of e.g. 20 Nanoliter), the meniscus is moving forward and at the end insulin will be replaced by air (cf. inlet 16i). As the dielectric constant of insulin is much larger than air, the capacitance will be decreased. This decrease in capacitance can be detected accurately by an electronic (not shown). This dependency is illustrated by FIG. 3.

Figure 3:
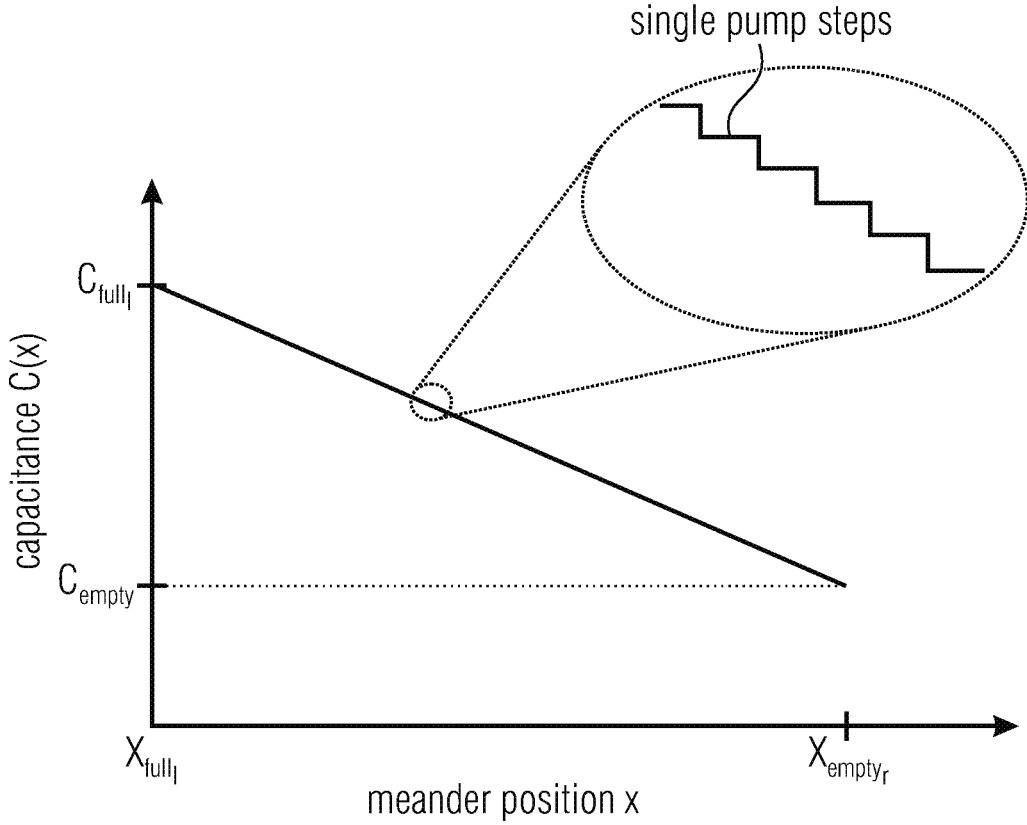
FIG. 3 shows a schematic diagram for illustrating the dependency between a capacitance signal and a fluid level according to embodiments.

FIG. 3 shows a diagram illustrating the capacitance c(x) plotted over the meander position x. Here, two positions $x_{fully}$ and $x_{empty}$ are illustrated together with $c_{fully}$ and $c_{empty}$. As can be seen by the enlarged view, the curve that has in the small view a substantially linear dependency comprises stairs. These stairs result from the single pump steps. Taking reference to FIG. 4a, 4b, the background for the detection of the amended position is shown.

FIG. 4a illustrates the system 10' attached to a body 20. As can be seen, the needle 12n extends into the body 20.

FIG. 4*a* shows the fluid level (and sealing level 15 within the reservoir 16 before a stroke, while FIG. 4*b* illustrates the fluid level 15' after a stroke.

The stroke volume dv complies to the insulin which is delivered into the body 20. As can be seen by FIG. 4*b*, the stroke volume dv is marked at two positions, namely at the needle 12*n* as insulin delivered to the body 20 and next to the inlet 16*i* as missing insulin level within the reservoir 16. This portion marked as stroke volume dv within the reservoir 16 as well as the portion having fluid 15' is monitoring using the electrodes 14 and 14*b*2. As discussed above, the insulin has a different dielectric constant when compared to the air. Due to the fact that air replaces the insulin at the portion marked by stroke volume dv within the reservoir 16, the capacitance has been changed. This capacitance change dc is marked. Due to the capacitance change, the meander position can be determined using the capacitance measurement device 14.

The air inlet 16*i* protects the drug 15/15' as will be discussed below.

The meniscus can only move without disturbance if no negative pressure is generated by this movement at the inlet. That principle needs a connection to the ambient air at the inlet of the meander. At the end of the meander the drug has contact to ambient air. The drug can be contaminated with kind of unwanted materials, like bacteria, viruses, poison molecules, etc. To avoid that contamination, the following strategy is chosen:

A hydrophobic filter 16*f* with small pore size (e.g. 0.2 μm) protects the inlet. These kind of filter have a high bubble point, due to the small pore size a pressure of more the 10 bar would be needed to press liquid through the filter. For that, neither liquids not bacteria or viruses can enter the inlet Additionally, an activated carbon filter 16*f* is arranged in series to the hydrophobic filter, which avoids that unwanted gaseous molecules like hydrocarbons can enter the inlet and get in touch with the drug at the end of the meander.

The meander shaped drug reservoir 16 is prefilled with drug. The inlet 16*i* is not only protected by a filter with small pore size and an activated carbon 16*f*, but also with a sealing, which is an airtight closing of the inlet. Thus, the filter is typically attached after filling.

For that, before the patient is using the patch pump, the drug is sealed from ambient, even from air. If the patient is using the patch pump, he removes the sealing. Beginning with that (sealing removing) time, the end of the meander has pressure contact to the environment, and can move, if the micropump is pumping For safety reasons, the system control can detect, if the sealing is removed (e.g. also by capacitive sensor, if a capacitance is changed, when the sealing is removed)

It has to be stated, that even if an unwanted gaseous molecule can pass all filters 16*f* and get in touch with the drug 15 it will be solved in the end of the meander, which has a length of about 100 millimeters (depending on the cross section of the channel and the desired overall drug volume in the reservoir). The diffusion time for that molecule is very long compared to the use time of the patch pump (approximately 7 days). Next, to reduce this risk furthermore, the patch pump should only use 80 . . . 90% of the drug, with that the end of the meander with some possible contamination will never be dosed into the patient.

According to embodiments the cross section of the track is in the range between 0.5 mm and 3 mm, advantageously 1 or 2 mm. The selected value is dependent on properties of the fluid, where in a smaller cross section of the tack enables a more accurate determination of a fluid level. Background is that a fluid change results in a large stroke along the meander track. Note the friction between the fluid and the track depends on the channel cross section.

Regarding the meander 16*m* within the reservoir 16, it should be noted that its shape is not important. The track can have a substantially square shape or a round shape or can also taper from the inlet 16*i* to the outlet 12*m*. Furthermore, instead of meander, a spiral shape can be used. Here, the so-called "LifeCoin" patch pump can be found. Just a bit modified, using the spiral instead of a meander and placing the pump 12 in the middle of the spiral, the LifeCoin can be formed.

The LifeCoin is prefilled with insulin, the meander spiral is made of class or plastics. Air inlet and needle outlet are covered by airtight sealings, which are removed by the patient before attaching the coin to the body.

The LifeCoin as well as the meander shape drug delivery system 10' advantageously comprises the capacitance measurement device before a special electrode design, here for example, three electrode portions enabling to control and monitor the system. For example, the design can be formed so as to enable a resolution of a signal stroke as discussed with respect to FIGS. 4*a* and 4*b*. Furthermore, according to embodiments, additional system control elements can be integrated, for example, a controller for the pump 12/12*p* activation, a dosing control and/or regulation. Furthermore, advantageously the patch pump comprises a battery which is not shown in the above embodiments. Additional sensors, like a glucose sensor can be optionally integrated at the needle 12*a* or in the needle 12*a* or behind the needle 12*a*. This enables a closed loop artificial pancreas, connection to a glucose sensor.

In that case (if a glucose sensor is adjusted at the needle 12*a*, no wireless data transmission (e.g. bluetooth) is needed to control the glucose level by adjusting the insulin dosing rate by the micropump. The system control has can not only monitor the pumping rate of the insulin, detect disturbances of the pump, but also adjust the blood sugar level by an appropriate control algorithm.

The entire system is very compact, flat and small and is working independently to control the blood sugar level. In that case, just a small display and/or alarm signal possibilities (acoustic, optical) to inform and show the patients the state of the working drug delivery system. Thus, the independent working can be arranged without a wireless data transmission unit (which needs a lot of energy and reduces weartime or needs large batteries).

It should be mentioned, that the system can be operated with a small amount of energy. Here a short consideration about the energy requirement of the micropump: the capacitance of the 3.5×3.5 mm$^2$ with 20 nl stroke volume silicon micropump is about C=1.5 nF, the voltage level (peak-peak is 100 V). To deliver 1 ml of reservoir, according to 1000000 nl, N=50000 pump strokes are needed to empty the reservoir. The efficiency of the electronics to generate the voltage is assumed to be just η=30% (as the voltage of a proposed flat battery is small, the efficiency is low).

In the following, the energy amount will be exemplarily calculated: For example, the overall energy the micropumps needs may be: E=N/η*½ C U$^2$. Thus this total energy needed for the pump amounts to E=2.5 Joule For comparison: Commercially available button cells have a typical end-of-life voltage of around 1.5V to 2V and capacities starting at ~5 mAh. The button cell Energizer 750 is sized D5.7 mm×1 mm and can store up to 36 J of energy. (The low continuous discharge current of these Batteries (typ. ~1 mA) can be stored in a capacitor which is then used to power the electronics only during pump/sensor actuation). Also, flat lithium cells can be used, for example a GEB201212C battery with a size of 1×12×12 mm³, a voltage rating of 3.6V and a capacity of 10 mAh (=130 mJ).

It should be mentioned that the drug delivery system should nearly the whole time in a "sleep mode", and will just be waked up during the desired amount of insulin has to be pumped. This enables a longer lifetime of the battery.

According to further embodiments, other drugs instead of insulin can be delivered, e.g., hormones, monoclonal antibodies or pain drugs.

According to further embodiments, the design of the pump 12 together with the reservoir 16 may have a flow restriction as free flow stop or a free flow stop. For this, the safety valve 12v may be important. Further the sealing protects the device during storage.

Below, additional features and especially advantages of the patch pump 10' will be discussed. According to embodiments, this patch pump would be on the one hand side much smaller compared to state of the art. It is so small, that it can be placed beyond the shirt without to be recognized from anybody else. Note, the patch pump is very accurate in dosing. Every pump stroke (of e.g. 20 nanoliter of a 3.5× 3.5×0.6 mm³ silicon micropump) can be resolved by the electronics. For that, even an accurate single stroke monitoring is possible. For example, the patch pump can perform any bolus which is needed for the patient, it is fully programmable.

According to embodiments, the patch pump exactly knows the filling status of the insulin, and can tell the user exactly about the remaining insulin until the next exchange. Note, due to the small size, even several patch pump systems can be stacked over each other or at the same plane, each patch pump with separate micropump, if it is needed that the patient not only needs one drug. For diabetes patients it is sometimes needed to decrease the blood sugar level with insulin or to increase the blood sugar level with another drug. Further embodiments enable evaporation of the drug: according to the vapor pressure of the drug, there is a small evaporation at the end of the meniscus through the inlet and the filters. This evaporation can be reduced, if a long air channel (diffusion stop) with small cross section (much smaller compared to the cross section of the meander channel where the drug is) is arranged between inlet and the beginning of the drug. With that, there will be a saturated atmosphere with drug molecule at the meniscus, and the evaporation will be very small. Due to the long channel, the drug molecules have a long way towards the inlet, the channel serves as a diffusion barrier. An advantage is that this patch pump is very safe. Catheter blockage, pump failure, needle dislocation, bubble entrance, glass break, all these failure modes can be easily and quickly detected by the electronics. Additional embodiments for failure detection are:

Pump failure (actuation): if the pump should make one pump stroke, and the meniscus does not move, the capacitance does not change=>failure Pump failure (valve): if the pump should make one pump stroke, and the meniscus does not move, the capacitance does not change=>failure Catheter blockage: if the catheter is blocked, the pump cannot push the drug forward, the meniscus cannot move=>failure With a separate electrode at the bottom side of the housing the system can recognize if the patch pump is attached to the skin. The system will only start to work if the patch pump is attached and keep to be attached.

With one separate safety electrode (e.g. placed immediately before or after the micropump) it can be easily detected, as the electrode can distinguish between drug and bubble. In normal case, at this electrode never a bubble should be. If the safety electrode detects a bubble=>failure Glass break or reservoir break: in that case, the capacitance is changing rapidly: =>failure Regarding the cost, it should be noted the current smallest silicon micropump has a chip size of 3.5×3.5 mm2, with a stroke volume of 20 nanoliter. With a production of 200 wafers per week, manufacturing cost of less than 40 cents for a tested pump chip seems to be feasible on the long term. We assume that all electronic components can be arranged in 1 or 2 specific ASICS. Together with an appropriate flat battery manufacturing cost (without insulin) of 2 . . . 3 € could be achieved on the long term at very high quantities, which could be a game changer in that market.

With respect to FIGS. 5a and 5b, the above-mentioned lifecoin will be discussed. FIG. 5a shows a side view/cross sectional view to the lifeCoin 10'', wherein 5b shows a top view to the lifecoin 10''. LifeCoin has a substantially round shape, wherein most of the area (cf. FIG. 5b) is used by the reservoir 16''.

In this embodiment, the reservoir 6'' comprises a track within which the fluid can be stored, wherein the track has a spiral shape, e.g., extending from the outside to the middle. The beginning of the spiral is marked by 16i'' representing the inlet, wherein the spiral ends at the micropump 12 which is arranged in the middle of the spiral. As can be seen, a needle 12n is attached at the bottom side of the unit 10''.

The components may be substantially comparable to the embodiments as discussed in the context of FIG. 1 and FIG. 2, wherein it may comprise some optional features.

In this embodiment, the reservoir 16'' comprises a solid metal or plastic cover, wherein on the top side of this plastic cover/reservoir 16'', the micropump and further elements, like a wireless communication (Bluetooth) element 22, a battery 24 or a controller 26 (here an ASIC for the micropump, sensor read out and/or dosing monitoring) may be arranged. The needle 12n on the button side of the reservoir 16'' may comprise a sealing.

Regarding the sizes, it should be mentioned that the entire system 10'' may have a diameter of 30 mm or 40 mm (range 20 mm to 60 mm) and a thickness of 4 to 5 mm and enables to store 1 ml insulin in the reservoir 10''.

Regarding the inlet 16i'', it is mentioned that this is combined with two filters 16f1'' (activated current filter) and 16f2'' (0.2 μm hydrophobic filter), a sealing for the air inlet 16s'' may be attached, e.g., at the top side of the unit 10''.

Below, an exemplary design of this lifecoin 10'' will be discussed, wherein the special focus is set on the capacitance measurement device. The capacitance changes for one single pump step amounts to:

$$\Delta C_{total} = \frac{(1 - \varepsilon_{insulin})\varepsilon_0 \varepsilon_{cover}{}^2 \Delta V}{(h_{channel}\varepsilon_{cover} + h_{cover})(h_{channel}\varepsilon_{cover} + h_{cover}\varepsilon_{insulin})}$$

With the parameter:

ΔV: stroke volume of the pump: 20 nl (of the 3.5×3.5×0.6 mm³ silicon micropump)

$\varepsilon_0$ dielectric field constant: 8.85 e-12

$\varepsilon_{insulin}$ relative dielectric constant of insulin: roughly 35 (depending on insulin)

$\varepsilon_{cover}$ relative dielectric constant of the cover (glass): 7 (depending on glass type)

$H_{channel}$: height of the insulin channel: 1.5 mm $H_{cover}$ height of both covers (glass): 0.6 mm $W_{channel}$: width of insulin channel: 1.5 mm $W_{wall}$: width of glass walls: 0.3 mm Reservoir Volume: 1 ml Note, that these parameters are just exemplarily assumed. With that, we get:

Capacitance change for one pump stroke (20 nl): 843 aF

Digisteps of (conventional) capacitance to Digital Converter for one pump stroke (20 nl): 14 steps: with that, a single pump stroke can be resolved easily.

Number of pump stroke volume for the entire reservoir: 50000 pump strokes

Entire Capacitance change: 42 pF $I_{channel}$: length of the spiral: 44.4 mm with this data we would have a diameter of the coin of 3.2 cm It can be noticed that the capacity change for one pump stroke depend on the height of the drug (e.g. insulin, and/or glucagon) channel. A reduction of the height result to an increase of that capacitance change (if all other parameters are constant). If the height is reduced, for example, from 1.5 mm to 0.75 mm, the capacitance change for one pump stroke of 20 nanoliter is increased from 843 aF to 1920 aF (according to about 31 digital steps of a typical commercial CDC converter/pump stroke), a reduction of the height to 0.5 mm result to a capacitance change of 2940 aF (according to 48 digital steps/pump stroke). That means, the reduction of channel height is a method to increase the sensitivity of the stroke volume measurement.

The channel height is an appropriate parameter to adjust the sensitivity of stroke volume measurement. Next, if the channel height is decreased, the capillary forces, which hold the meniscus in a stable position (mainly independent from gravitation) are increasing.

On the other side, there are also drawbacks making the channel height smaller, especially the length of the channel has to be increased to realize a certain drug reservoir volume (e.g. 1 ml for a U1000). This increase of channel lengths has the following drawbacks:

1) the lateral space for the reservoir has to be increased, for a 1 ml reservoir (and 1 mm wall thickness between the channels) the coin diameter for the spiral shaped reservoir in increased from 3.8 cm (1.5 mm channel height) to 5.3 cm (0.75 mm channel height) to 6.5 cm (0.5 mm channel height).

2) If the channel height is reduced, the friction to move the meniscus, if the pump is active, is increasing rapidly according laminar friction laws.

That can be partly improved, if the width of the channel is increased, e.g. from 1.5 mm to 2 mm or 3 mm. However, the with should not be too large to ensure a defined movement of the meniscus, if the pump is actuated.

For that reason, looking to a 1 ml reservoir size of a U1000 insulin, a channel height of 1 mm or 1.5 mm might be a good compromise between resolution of the capacitance stability, the stability of the meniscus, the lateral size of the reservoir and the laminar friction of the moving liquid in the channel.

For other reservoir sizes (e.g. a 0.3 ml reservoir) smaller channel heights or other geometries might me better to fit to other geometries.

In the future, if new high concentrated drugs might be developed, even smaller reservoir sizes of e.g. 0.1 ml or even less might be used. In that case, the channel height can be reduced furthermore to a value of 0.5 mm or 0.1 mm, the capacitive signals get even higher, enabling the accurate dosing of very small quantities (e.g. 10 nanoliter or 1 nanoliter or less) with future micropumps having smaller stroke volumes than 20 nanoliter.

According to embodiments the cross-section in at least one dimension amounts to 2.8 mm or 3 mm, or smaller: for example 3 mm×3 mm or 2.8×2.8 or 4 mm×2 mm or advantageously 1.5 mm×1.5 mm or 2 mm×1.5 mm or 1.5 mm×1 mm, etc. Here, at least one dimension should by smaller than the 3 or 2.8 mm in order to maintain the meniscus in the reservoir. Background will be discussed base on the following formula:

$$\frac{F_\sigma}{F_z} = \frac{\sigma l_{typ}}{g\rho l_{typ}^3} = \frac{\sigma}{g\rho} \cdot \frac{1}{l_{typ}^2} >> 1$$

$$l_{typ} << \sqrt{\frac{\sigma_{Wasser-Luft}}{g\rho}} = 2.8\text{mm}$$

Here, the interface surface energy $\sigma$ is defined as $\sigma=dE/dA=dF/ds$. $\sigma_{Wasser-Luft}$ is the interface surface energy between water and air. The 2.8 mm are valid for water surrounded by air. Based on this calculation it can be concluded that for small structures (smaller than 2.8 mm in at least one dimension the interface surface force is larger than the gravity, so the meniscus will be maintained. In order to have a reserve e.g. for the case of shaking the at least one dimension can be smaller than 2.0 mm or 1.5 mm.

According to embodiments, the lifecoin" may be implemented as a closed loop system, e.g., artificial pancreas in a lifecoin:

With the usage of up-to-date real time glucose sensors (e.g. Dexcom G6) the lifecoin becomes a closed loop system, enabling diabetes patients to have a normal life without worrying about glucose measurements.

The sensing element might either be integrated into the Lifecoin directly (only one device, but dose to insulin dosing area) or connected via wireless communication With adjusted controlling algorithms (e.g. AI) a safe and comfortable solution for diabetes patients could be provided The same principle would work for other chronic diseases, where a sensor is available Below, the electrode design and the functionality will be discussed, wherein it should be mentioned that here optional elements of this capacitance measurement device are mentioned. The capacitance measurement device may be arranged as electrodes arranged on the top side and the bottom side of the reservoir 16", but is not shown within the view of FIGS. 5a and 5b.

For capacitance measurement different electrode arrangements are possible. The standard approach consists of two parallel electrodes on top and on the bottom of the reservoir 16r (common parallel plate capacitor design).

Another exemplary possibility are two coplanar electrodes only on one side of the reservoir 16". This design is potentially cheaper to manufacture but more complex methods are needed for electronic field calculations and for disturbance avoidance (e.g. a CND-electrode shielding the design).

Independent of the chosen electrode arrangement it is possible to use multiple electrodes to divide the reservoir in multiple sub-areas, or use two electrodes in parallel to get a double-controlled measurement of the reservoir level.

The capacitance measurement is a critical component of the lifecoin design 10". In theory it is possible to detect capacitance changes even for singular pump strokes. In reality there are many external and internal disturbances that can hinder correct capacitance measurement: Capacitance change due to temperature or external E-fields, interference with "patent ground/patient noise" and also sensor drift. To compensate for these effects, precautions may be taken:

Shield measurement electrodes against external disturbances by using covering shields on top/bottom;

Provide means of disturbance measurement and estimation, e.g. a dedicated "static" electrode used for drift correction; and for Use a "Zeroing before actuation" strategy, where the capacitance is set to zero immediately before pump actuation to remove drift effects Common CDC chips have multiple capacitance measurement channels. While most channels are most likely used for liquid level detection, some can be utilized to gain additional functionality. Dedicated electrodes can be used for example for;

Bubble detection

Drift detection and compensation

Fluid permittivity detection (Electrode with accurately defined area and distance), maybe this even allows to check whether or not the used insulin is spoiled (in case the pre-filled unit is stored for a longer time or was exposed to radiation or similar)

Detect meniscus movement after the pump (to enable auto-filling when the patient unseals the system)

Detect when the seal/outer cover is removed

According to embodiments, a modular design for improved sustainability may be used. It is possible to build a more sustainable and possibly cheaper lifecoin by using a modular system design. In this approach the electronics (Pump driver circuit 26, battery 24, CDC IC 36) are separate from the fluidics (meander with electrodes, pump and needle). The pump itself is part of the disposable part, and because of that, there is no need for a complicated fluidical/mechanical interface between these two sub systems. The only connections used between electronic and fluidic part are (two) electrical connections between micropump 12 and pump driver 26 some more electrical tracks connecting the CDC chip 26 and the electrodes on the fluid reservoir 16r.

This is a huge difference (and possible advantage) to "syringe/plunger-type" dosing systems, where a reservoir change implicates an initial filling step to bring the plunger in contact with the new reservoir and during this step, the system can either lose some drug or over-dose the patient.

The modular design reduces waste and possibly reduces overall system cost, since the costly electronics part can be reduced.

Additional functions can be realized when using a modular design, e.g. the needle could automatically be advanced mechanically when the electronics part is attached.

The overall system can keep its very flat shape even with the modular design.

Furthermore, it should be noted that for the channel manufacturing, the following tolerance calculation may be taken into account:

How depending on the change of (calculated) pump volume from variations of the other parameter (e.g. channel height):

$$\frac{\Delta(\Delta V)}{\Delta V} = \frac{((2h_{channel}\varepsilon_{cover}h_{cover}(\varepsilon_{insulin}+1)))\varepsilon_{cover}\Delta h_{channel}}{(h_{channel}\varepsilon_{cover}+h_{cover})(h_{channel}\varepsilon_{cover}+h_{cover}+h_{cover}\varepsilon_{insulin})}$$

Qualitative discussion: since $h_{channel}$ is present in the formula in a squared form, a variation of $h_{channel}$ will cause double an error in the stroke volume.

When assuming a reproducibility (no individual calibration of LifeCoin) of 10%, the tolerance in the channel height should not be greater than 2-3%. This applies in analogy to the variations concerning the glass cover. The dielectric constants and the capacity are only present in a linear form and consequently tolerances of roughly 4-6% are acceptable for these parameters. (All the contributions are squared and added in connection with the square root.)

If (like in the preceding example) the channel height is 1 mm and the thickness of the cover is 0.3 mm, the channel height should not vary by more than 20-30 μm and the lid thickness by not more than 6-9 μm.

The intensity of the variation of the dielectric constants is dependent on the production method of the insulin. It would be conceivable here for this parameter to be measured with each batch and transferred to the system controller.

From the above considerations, it seems to be obvious to use a glass plate having a highly defined thickness and then to completely shape the meander spiral. This entails using two covers having highly defined thicknesses. The spiral is capped using these two (patterned) covers by means of bonding. Then, the covers comprise the throughways for the insulin at the inlet and the outlet.

Note, according to embodiments, it is advantageous for the safety and the free flow protection to use a "brickle" reservoir like glass.

The advantage of a glass structure is that the user can hardly generate overdosing by applying a force onto the reservoir. Whereas, in the case of a flexible bag, the same may be deformed and the overpressure involves the danger of overdosing, the glass reservoir would break and therefore no overpressure can form.

The only danger entailed is the situation when a patient is approaching ground in a plane. The human body needs a few breaths to compensate the pressure, the result being a slight difference in pressure. This difference in pressure may cause slight overdosing.

Danger would result, for example:

if the patient suddenly entered a hyperbaric chamber and was given artificial respiration using an oxygen cylinder, for example, or if an overpressure was generated intentionally using the LifeCoin by placing a bell jar over the LifeCoin, for example, and pumping it up. The result would be free flow.

Regarding the free flow protection, embodiments according to variant 1: This potential malfunction can be avoided using a safety valve 12v (e.g. using a known FhG patent of 2007, and as shown in FIG. 2). This safety valve is advantageously integrated in the silicon pump chip. It is configured such that the maximum free-flow leakage rates, for the duration of an (assumed) erroneous overpressure, are not higher than the bolus rates of the application.

Embodiments according to variant 2: A flow restriction (in the pump silicon or in the reservoir meander (glass or plastic)) configured such that even the worst-case overpressures (in an airplane or when willfully applying an overpressure) do not administer a harmful dose, may be sufficient. This restriction could be a narrow cross section in the path of the drug.

According to embodiments, the flow restriction may be implemented as a filter directly in front of the pump so as to protect the pump from insulin crystals or other contaminations.

Note that dependent on the risk assessment, a safety valve may be beneficial.

According to embodiments, the disturbance parameter detection can be performed as follows:

A constant skin temperature of roughly 32° will result in similar viscosity characteristics of the medium. When the pump is not degraded over the short application period (or the degradation is definable), a change in the media viscosity can be detected (→degradation of the insulin), or clogging of the fluid line (→occlusion or extravasation) since more pump strokes are used for the same delivery volume.

Detection of different types of insulin using different permittivities and consequently resulting capacities and delivery rates adapted thereto (like recognizing that erroneously U1000 insulin was used instead of U100 insulin)

Regarding the electrode design, it should be noted that according to further embodiments, one or more of the following principles may be used:

Finger-shaped electrodes following the meanders for reducing the overall capacity and the "disturbance capacity" caused by the channel walls Using a planar "single-sided" electrode with no counter-electrode for easier production Here, a new capacity computation may be used: plates next to each other instead of opposite to each other, like: . . . or . . . , otherwise a simulation is used in the case of more difficult constellations (in particular different ER)

Shielding from ground (skin of the patient) at the lower side/bottom of the patient in order to keep disturbance influences low Maybe a dedicated drift-detection electrode in a region filled with fluid (and maybe another one in a complete free region) to be able to better subtract the drift Sub-division into several electrodes to be able to use several channels of the measuring IC Either provide electrodes in portions (like one electrode per 20% of the channel length=5 electrodes→dividing the overall capacity)

Or two (or more) parallel electrodes mutually monitoring themselves or the fill level Another electrode etc. can be used to recognize ripping of the sealing Additional electrode BEHIND the pump (and/or close to the needle)

Determine when the pump is filled (either in the patient or the factory when pre-filling the reservoirs)

To detect body liquid, if back flow occurs (body liquid has another dielectric constant compared to insulin)

Starting from this electrode, there is a precisely defined volume (of the syringe) before the meniscus reaches the patient Regarding the modular design, it should be noted that according to embodiments, a further cost reduction is possible, when designing the electronics (pump driver, battery and, maybe, capacity IC) to be separable. These do not contact the patient/insulin and can be re-used. Disadvantageously consumes slightly more space but is more sustainable.

Note, installing an additional flow restriction in the fluid-containing part of the channel:

Additional safety in case an overpressure in the reservoir should form for some reason (lower flow rate)

Hardly disturbs the pump operation due to the low frequencies effect: at the same time protects the pump from crystals/particles in the insulin and is fail-safe: in case air is sucked in, it will be caught in the filter Regarding the surface characteristics, it should be noted that according to embodiments an (idle) netting angle of 90 degrees (in general range between 75°-105° or between 60° and 120° or between 45° and 135°) between insulin and the channel may be used for best meniscus forming. Background thereof is that evaporation/condensation influence can have an influence on the sensor resolution, especially for periods of days to weeks. The above-mentioned wetting angle of 90 degrees or something around 90 degrees, 75-105 may be used. Regarding sensor drift, it should be noted that according to embodiments, the known concept of "zeroing before actuation" can be applied to minimize the drift effects.

Regarding the shape of cross section of the meander/spiral/track: The shape of the cross section is influencing, whether or not insulin will remain in the corners. Round or elliptic would be the best, but possibly difficult to manufacture. Thus, according to embodiments round edges would be advantageous. But even if insulin is remaining in sharp corners of the cross section (e.g. rectangular cross section), this can be handled: If the remaining insulin in sharp corners is constant, this can be considered as a constant offset.

Furthermore, the inner surface of the meander channel may according to embodiments be smooth. If the roughness is too high, the meniscus has to change the shape at this microscopic roughness according to the wetting angle by moving forward. This change of shape is analogous to a (small) capillary pressure, which might influence the accuracy and reproducibility of the measurement of a single pump stroke. If the roughness is small enough (e.g. smaller than 1 μm), the meniscus can move forward without having any significant obstacles.

But even with higher roughness, the capacitive dosing monitoring will work, just variations in single pump stroke measurements will occur. Over a quantity of 50 pump stroke of 20 nanoliter of a silicon micropump to achieve 1 Unit (according to 1 μl) of an U1000, the error du to surface roughness should not be significant.

The process for connecting the drug delivery system with the patient can be supported by additional devices. For high reliably of the connection, a kind of needle may be used to get through the outer skin into deeper areas, where it can stay. To reduce stress from a stiff needle, the needle is normally only used for penetration and then rejected leaving only a non-rigid dosing end inside the body. For this procedure a certain apparatus is advantageous. Continuous blood glucose sensors use a handheld device, which a patient puts onto the skin, pushes a button and the needle inserts a drug delivery tube while gluing the patch onto the skin. Afterwards the sensor electronics is clicked onto the patch and the sensor is ready to operate.

A similar system can be imagined for the above discussed drug delivery system here: The fluid part is glued onto the skin while injecting a drug delivery tube. All fluidic parts are already placed (no open areas where contamination could occur) and the (reusable) electric part (battery, pump driver, transmitter, and logic) is inserted afterwards. A strained spring releases the needle after pushing the button, opens the skin for a micro-tube that is connected to the micropump outlet (and initially to the needle). Whilst the needle retracts immediately, the micro-tube loses its connection and stays beneath the skin.

According to embodiments the drug delivery system may comprise two reservoirs (side by side, layer by layer or combined) for two different drugs. For example, the drug delivery system consisting of two lifecoins, one filled with Insulin and one with Glucagon (the opposite hormone to insulin). The first ensures keeping blood sugar low, whereas the latter stops Insulin from working, if blood sugar reaches dangerously low ranges. This may happen due to a patient doing sports or skipping a meal. With both pumps and a glucose sensor a real artificial pancreas can be created (this is already done with other pumps). Glucagon is also available in reasonable small cartridges and can be handled similarly as Insulin. The controlling which drug is delivered can be done by a controller connected to a glycose sensor.

Instead of two lifecoins a system can be realized having two separate meander shaped reservoirs (one filled with Insulin and one with Glucagon) on one layer, each reservoir having one micropump to deliver independently either insulin or glucagone. Both pumps can be placed in the middle of the coin. In this embodiment, there could be attached either two different needles or catheters to deliver either insulin or Glucagobe, or within the lifecoin channel system there is a Y junction between the outlet of the two pumps and the outlet to the needle, where the drug (either Insulin or Glucagon) is delivered.

To save manufacturing cost and/or packaging cost, the two micropumps (e.g. the 3.5 mm$^2$ silicon micropump developed by the Fraunhofer EMFT, both pumps have an integrated safety valve) can be diced from the wafer in one piece (size 3.5×7 mm$^2$) and mounted (e.g. glued) to the channel system (with the two meander for Insulin and Glucagove)

Although some aspects have been described in the context of an apparatus, it is clear that these aspects also represent a description of the corresponding method, where a block or device corresponds to a method step or a feature of a method step. Analogously, aspects described in the context of a method step also represent a description of a corresponding block or item or feature of a corresponding apparatus. Some or all of the method steps may be executed by (or using) a hardware apparatus, like for example, a microprocessor, a programmable computer or an electronic circuit. In some embodiments, some one or more of the most important method steps may be executed by such an apparatus.

Depending on certain implementation requirements, embodiments of the invention can be implemented in hardware or in software. The implementation can be performed using a digital storage medium, for example a ROM, a PROM, an EPROM, an EEPROM or a FLASH memory, having electronically readable control signals stored thereon, which cooperate (or are capable of cooperating) with a programmable computer system such that the respective method is performed. Therefore, the digital storage medium may be computer readable.

Some embodiments according to the invention comprise a data carrier having electronically readable control signals, which are capable of cooperating with a programmable computer system, such that one of the methods described herein is performed.

Generally, embodiments of the present invention can be implemented as a computer program product with a program code, the program code being operative for performing one of the methods when the computer program product runs on a computer. The program code may for example be stored on a machine-readable carrier.

Other embodiments comprise the computer program for performing one of the methods (determining a disturbance, controlling the pump, e.g. dependent on a sensor signal or an external command) described herein, stored on a machine-readable carrier.

In other words, an embodiment of the inventive method is, therefore, a computer program having a program code for performing one of the methods described herein, when the computer program runs on a computer.

In some embodiments, a programmable logic device (for example a field programmable gate array) may be used to perform some or all of the functionalities of the methods described herein. In some embodiments, a field programmable gate array may cooperate with a microprocessor in order to perform one of the methods described herein. Generally, the methods are advantageously performed by any hardware apparatus.

While this invention has been described in terms of several embodiments, there are alterations, permutations, and equivalents which fall within the scope of this invention. It should also be noted that there are many alternative ways of implementing the methods and compositions of the present invention. It is therefore intended that the following appended claims be interpreted as including all such alterations, permutations and equivalents as fall within the true spirit and scope of the present invention.

The invention claimed is:

1. Drug delivery system comprising:
at least one reservoir comprising a meander shape or spiral shape, the reservoir comprising an inlet and a filter;
a measurement device configured to determine a parameter of the at least one reservoir; and
at least one micropump configured to deliver a fluid from the reservoir to an outlet;
wherein the filter is arranged at the inlet and configured to allow air flowing into the reservoir when the fluid is delivered out of the reservoir;
wherein the measurement device is implemented as capacitance measurement device comprising two electrodes arranged with the reservoir inbetween, wherein the reservoir and/or a fluid within the reservoir acts as a dielectricum;
wherein the capacitance measurement device is configured to determine a dielectric constant and/or capacity, wherein the dielectric constant and/or, wherein the capacity is dependent on a fluid level of the reservoir;
wherein comprising a control configured to determine the fluid level based on a capacitance signal determined by the capacitance measurement device;
wherein the control is configured to detect using the capacitance signal determined by the capacitance measurement device at least one of the following: catheter blockage, pump failure or glass break.

2. Drug delivery system according to claim 1, wherein the control is configured to detect a needle dislocation, a bubble entrance, intrusions, a disturbance of the micropump or an open inlet.

3. Drug delivery system according to claim 1, where a pump failure is detected, if the pump should make one pump stroke, and the capacitance signal does not change;

where a catheter blockage is detected, if the pump cannot push the drug forward, so that the capacitance signal does not change;

where glass break or reservoir break is detected in that case, the capacitance signal is changing rapidly.

4. Drug delivery system according to claim 1, wherein the reservoir is prefilled with a fluid or a drug.

5. Drug delivery system according to claim 1, wherein the filter comprises a hydrophobic filter or an activated carbon filter or a hydrophobic filter and an activated carbon filter arranged in series or another filter or filter combination configured to filter viruses and/or bacteria.

6. Drug delivery system according to claim 1, wherein the inlet comprises a sealing.

7. Drug delivery system according to claim 1, wherein a housing of the reservoir is formed by glass or polymer; and/or wherein the meander shape or spiral shape comprises a track extending from the inlet to an opening for the micropump.

8. Drug delivery system according to claim 1, wherein each of the two electrodes is separated into two or more portions; or wherein each of the two electrodes is separated into two or more portions in order to increase the resolution for detecting a fluid level or to determine disturbance.

9. Drug delivery system according to claim 1, further comprising a control which is configured to determine a stroke volume during the operation of the micropump based on a capacitance signal or a change of the capacitance signal determined by the capacitance measurement device; or further comprising a control which is configured to determine a stroke volume based on a capacitance signal or a change of the capacitance signal determined by the capacitance measurement device during operation of micropump delivering the fluid by use of a single stroke or multiple strokes.

10. Drug delivery system according to claim 1, further comprising a control which is configured to determine a disturbance within the reservoir or a disturbance of the micropump or a disturbance of the drug delivery system or to detect an open inlet or to determine a partial closing or closing of a needle or tube, to determine air or a particle within the reservoir or to determine leaking of the reservoir or evaporation from the reservoir or to determine a reflow.

11. Drug delivery system according to claim 1, wherein the capacitance measurement device comprises a third electrode which is attachable to the skin in order to recognize if the drug delivery system is correctly attached to the skin; and/or wherein the electrode of the capacitance measurement device comprises at least two portions portion which is arranged before and/or behind the micropump in order to distinguish between drug and bubble.

12. Drug delivery system according to claim 1 comprising a second reservoir or a second reservoir in combination with a second micropump in order to deliver another fluid from the second reservoir to an outlet;

comprising a second reservoir forms as further meander or spiral together or next to the meander spiral in order to deliver another fluid from the second reservoir to an outlet.

13. Drug delivery system according to claim 1, wherein a needle, a catheter or a tube is attached to the outlet.

14. Drug delivery system according to claim 1, further comprising a sensor or glucose sensor, which is contact to a body liquid via an own catheter or via a needle, a catheter or a tube of the drug delivery system; or further comprising a sensor or glucose sensor which is contact to a body liquid via an own catheter or via a needle, a catheter or a tube of the drug delivery system in combination with a control.

* * * * *